(12) United States Patent
Guttman (10) Patent No.: US 7,321,423 B2
(45) Date of Patent: Jan. 22, 2008

(54) REAL-TIME GONIOSPECTROPHOTOMETER

(75) Inventor: Jeffrey L. Guttman, Los Gatos, CA (US)

(73) Assignee: Photon, Inc., San Jose, CA (US)

( * ) Notice: Subject to any disclaimer, the term of this patent is extended or adjusted under 35 U.S.C. 154(b) by 269 days.

(21) Appl. No.: 10/915,204

(22) Filed: Aug. 9, 2004

(65) Prior Publication Data

US 2005/0062964 A1 Mar. 24, 2005

Related U.S. Application Data

(60) Provisional application No. 60/495,132, filed on Aug. 15, 2003.

(51) Int. Cl.
*G01J 3/42* (2006.01)

(52) U.S. Cl. ........................... 356/319; 356/328

(58) Field of Classification Search ......... 356/319–330
See application file for complete search history.

(56) References Cited

U.S. PATENT DOCUMENTS

| | | | |
|---|---|---|---|
| 4,329,050 A | 5/1982 | Olsen | |
| 4,712,914 A | 12/1987 | Cross et al. | |
| 6,108,083 A * | 8/2000 | Machler | 356/328 |
| 6,249,751 B1 * | 6/2001 | Asaba et al. | 702/76 |
| 7,167,246 B1 * | 1/2007 | Skierski | 356/408 |
| 2003/0030011 A1 * | 2/2003 | Brown et al. | 250/455.11 |

FOREIGN PATENT DOCUMENTS

JP 05072033 A 3/1993

OTHER PUBLICATIONS

Great Britian Search Report from Application No. GB0418269.7 dated Nov. 19, 2004.

* cited by examiner

*Primary Examiner*—Layla G. Lauchman
(74) *Attorney, Agent, or Firm*—Finnegan, Henderson, Farabow, Garrett & Dunner, L.L.P.

(57) ABSTRACT

In accordance with embodiments of the present invention, a goniospectrophotometer is provided for quickly obtaining a goniospectrum using a goniospectrophotometer. In some embodiments, a parabolic reflector is used to optically transform the angular space of a source at the parabola focus into a linear space and facilitate the use of a single diffracting element and area camera to simultaneously measure the angular spectrum of the source. Spectra corresponding to zenith angles of light reflection by the parabolic reflector can be acquired by a detector and analyzed in a computer.

30 Claims, 6 Drawing Sheets

REAL-TIME GONIOSPECTROPHOTOMETER

RELATED APPLICATIONS

The present application claims priority to provisional application 60/495,132, entitled "Novel Real-Time Goniospectrophotometer" by Jeffrey L. Guttman, filed on Aug. 15, 2003, herein incorporated by reference in its entirety.

BACKGROUND

1. Field of the Invention

The present invention is related to the use of goniospectrophotometric, goniospectroradiometric, goniophotometric, or gonioradiometric measurements of primary or secondary sources, including the fields of color measurement, scatterometry, multi-angle light scattering (MALS), and beam profiling.

2. Discussion of Related Art

Goniospectrophotometers are used for characterizing the spectra of light as a function of angle for light sources such as LEDs, and also for materials painted or printed with gonioapparent or pearlescent pigments in the paint and ink. Conventional commercially-available systems obtain the goniospectra either by using an optical fiber coupled spectrophotometer and moving the fiber about the source or sample, or by using a set of spectrometers positioned at a set of fixed angles. Measurement times for multiple zenith angles at a single azimuth angle about the source are typically in the range of 1-20 minutes.

Figure 1:
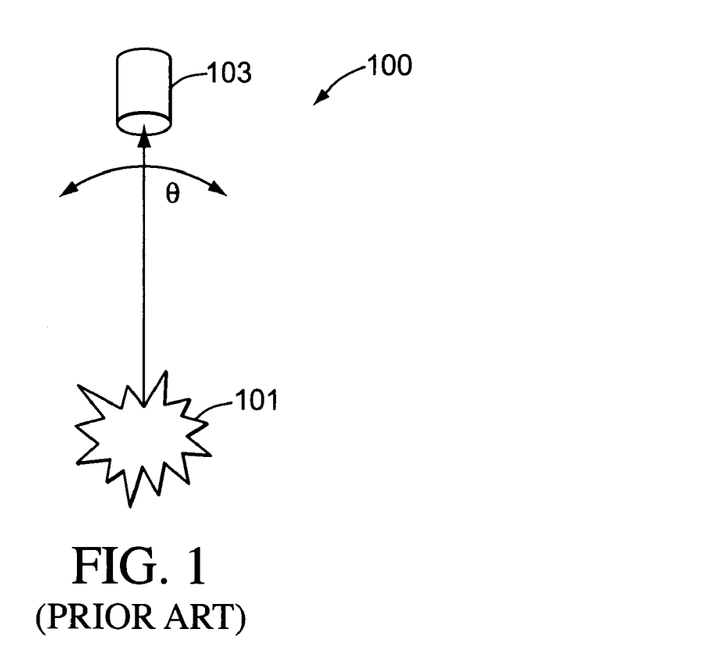
FIG. 1 illustrates an embodiment of a goniospectrophotometer where a detector system is scanned around a light source.

Conventional practice uses mechanical scanning of a detection system (such as a fiber-coupled spectrograph) about the source. FIG. 1 shows a schematic diagram of a conventional Goniospectrophotometer 100. Detection system 103 of goniospectrophotometer 100 can, for example, be a fiber-optic cable attached to a spectrophotometer to provide spectral data regarding light source 101. As such, detector system 103 is highly directional in its receipt of optical radiation from source 101 and therefore can be configured to receive light at substantially a single zenith angle at a single azimuth angle from light source 101. The distance between detection system 103 and light source 101 is typically within the "near-field" region, but may also be in the "far-field" region. The "far-field" region is characterized by a distance far enough from light source 101 such that light source 101 can be viewed as a point source. A commonly used rule of thumb boundary between the two regions is the "Five-Times Rule," where detection system 103 is placed at a distance from light source 101 that is at least five times the lateral extent of light source 101.

In operation, detector system 103 is scanned around light source 101 stopping at each of a set of predetermined zenith angles to measure a spectrum with a spectrometer. Thus, a spectral scan as a function of angular position for a single azimuth angle around light source 101 is obtained. In some embodiments, detector system 103 can be rotated along a great circle on a sphere with light source 101 at its center. Detector system 103 can also be oriented so that it collects light in a small solid angle substantially originating from the center of the sphere.

Figure 2:
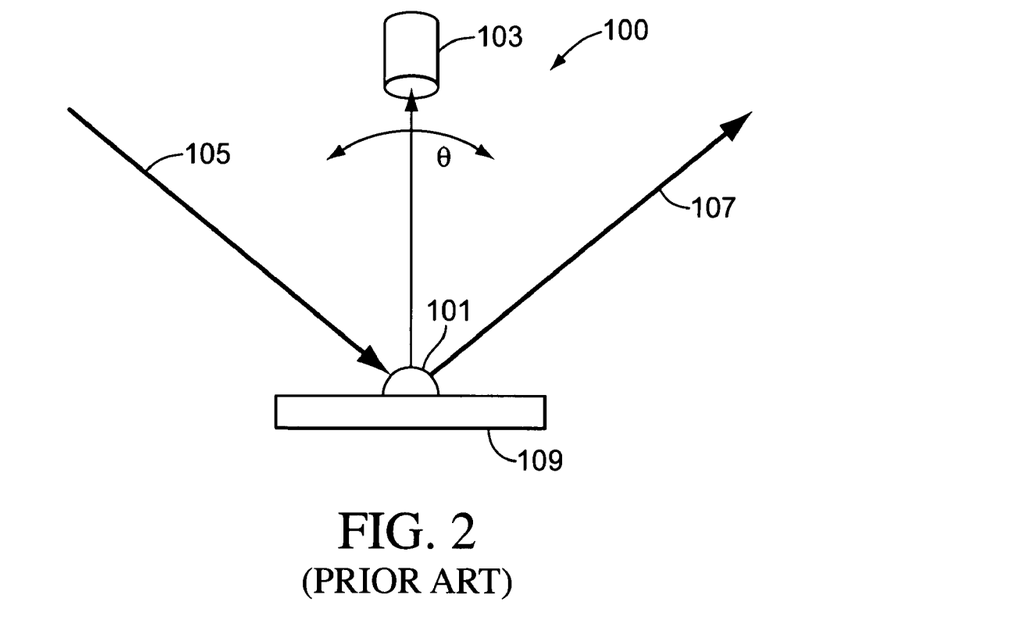
FIG. 2 illustrates an embodiment of a goniospectrophotometer as illustrated in FIG. 1 where the light source is an illuminated material.

FIG. 2 illustrates an example where source 101 is illuminated by light beam 105. Light beam 107 is a reflection from light source 101 of illuminating beam 105. As shown in FIG. 2, light source 101 may be a material deposited on a base or substrate 109. In some testing situations, scatter of light beam 105 is measured in detector system 103. In some testing situations, light from light source 101 is a result of luminescence after excitation by illuminating light beam 105.

Performing a spectral scan at each angular position, however, takes a significant amount of time to perform. Therefore, systems such as those shown in FIG. 1 and 2 can be very slow. As mentioned above, a spectral scan at an individual azimuth can take up to about 20 minutes. Therefore, an angular distribution of that scan can involve a few hundred to a few thousand minutes (depending on the number of angles) to execute.

Figure 3:
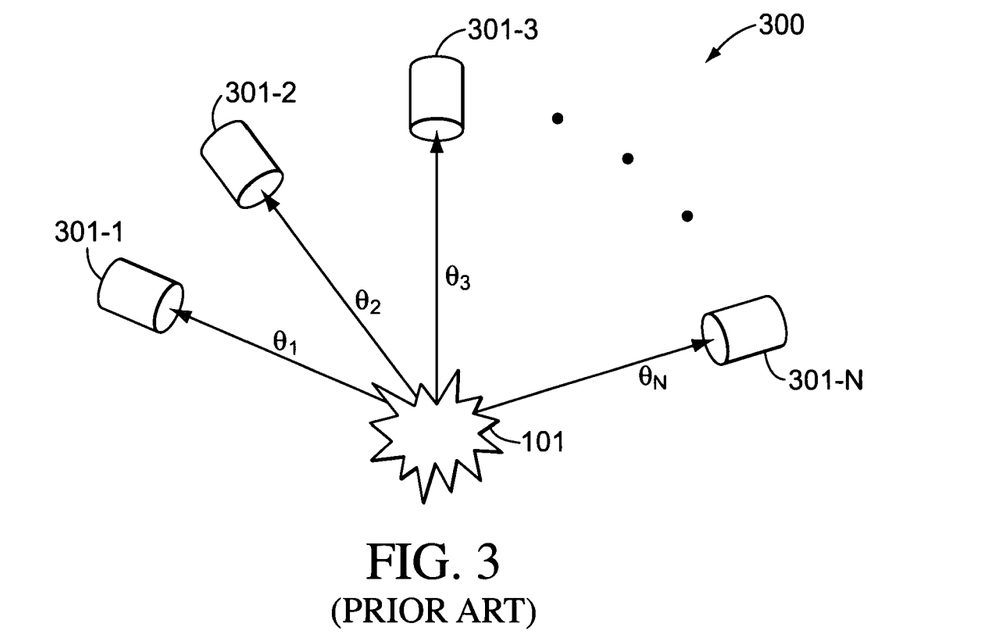
FIG. 3 illustrates an embodiment of a goniospectrophotometer that includes multiple detectors/spectrometers located at fixed angles about the light source.

FIG. 3 illustrates a goniospectrophotometer 300 that mitigates the scanning time somewhat. As shown in FIG. 3, goniospectrophotometer 300 includes a plurality of detector systems 301-1 through 301-N. Detector systems 301-1 through 301-N are fixed at particular angles around light source 101 so that each receives light from light source 101 at a particular zenith angle $\theta_1$ through $\theta_N$. As described above, each of detector systems 301-1 through 301-N can include an optical fiber directed to receive light at an azimuthal angle $\theta_1$ through $\theta_N$ from light source 101. Each of detector systems 301-1 through 301-N can include a spectrometer for providing a spectrum at the corresponding one of zenith angles $\theta_1$ through $\theta_N$.

Figure 4:
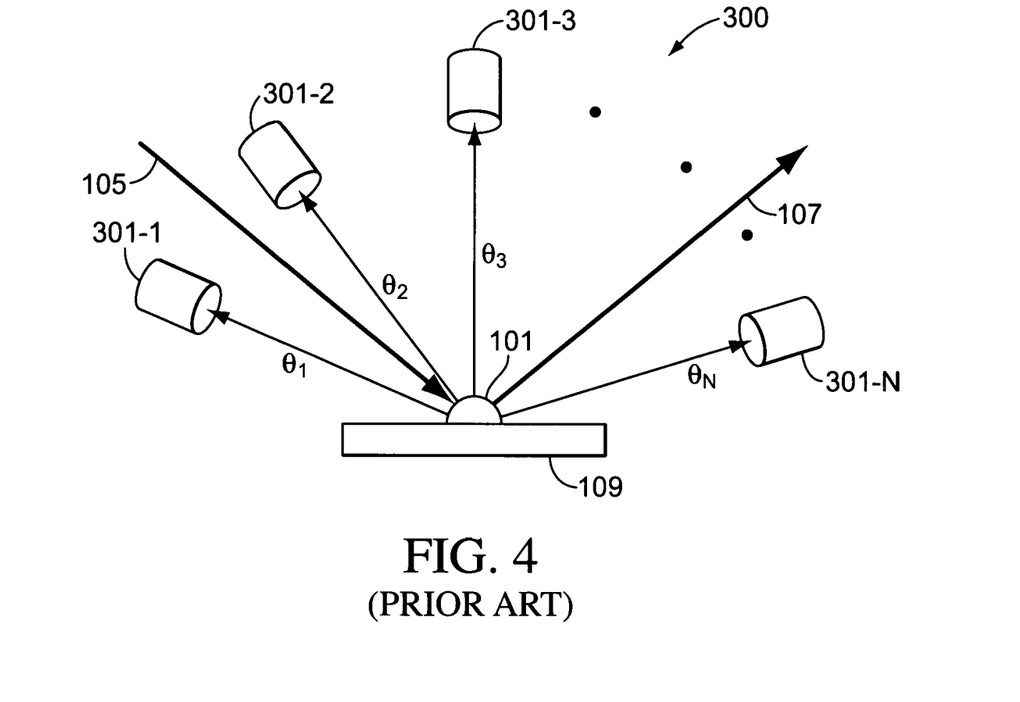
FIG. 4 illustrates the embodiment of goniospectrophotometer shown in FIG. 3 where the light source is an illuminated material.

FIG. 4 illustrates a goniospectrophotometer 300 utilized to characterize a light source 101 illuminated by beam 105. Light source 101, which can be on substrate 109, reflects, luminesces, or otherwise emits light in response to illumination beam 105. Illumination beam 105 is reflected from light source 101 into reflection beam 107.

Although the embodiments of goniospectrophotometer 300 shown in FIGS. 3 and 4 reduce the amount of time required to provide a spectral scan of light source 101, they are expensive in that each of detector systems 301-1 through 301-N is an independent detector system that requires an independent spectrometer. Further, goniospectrophotometer 300 suffers from the need to calibrate multiple detector systems 301-1 through 301-N. Also, there may be difficulty in measuring continuous angular spectra due to mechanical obstructions from mounts utilized to hold other detector systems 301-1 through 301-N in place.

Therefore, there is a need for economical, faster methods of obtaining the angular dependence of color spectra of light from material samples or light sources for applications requiring goniospectrophotometric analyses.

SUMMARY

In accordance with the present invention, a goniospectrophotometer includes a parabolic reflector that allows for optical transformation of the angular space of a light source at the parabola focus into a linear space. A single diffracting element and area camera can then be utilized to simultaneously measure the angular spectrum of the source.

A method of obtaining an angular spectrum according to some embodiments of the present invention includes parabolically reflecting light from a light source to provide a beam of light, the beam of light including light from a range of zenith angles at a particular azimuthal angle from the light source; spectrally dispersing light from the beam; and capturing a goniospectrum corresponding to the beam, the goniospectrum including spectra corresponding to the range of zenith angles. In some embodiments, the beam of light includes a set of discrete beams, each beam in the set of discrete beams corresponding to a zenith angle in the range of zenith angles. In some embodiments, the set of discrete beams may be collimated. In some embodiments, spectrally dispersing light from the light beam includes diffracting the light beam in a diffraction grating. In some embodiments, the beam may be focused before being spectrally dispersed. In some embodiments, capturing a goniospectrum includes detecting a spectrum from the diffraction grating corresponding to a plurality of zenith angles within the range of zenith angles. In some embodiments, the spectrum is a zero'th order spectrum, although a higher order spectrum may be utilized. In some embodiments, the spectrum from the diffraction grating can be projected on a screen. In some embodiments, detecting the spectrum includes digitally capturing an image of the spectrum in a digital camera. The camera may be a CCD array. In some embodiments, the light source can be a sample illuminated by an illumination beam. In some embodiments, the illumination beam results from a source of light coupled to the same through an optical fiber.

A goniospectrophotometer according to some embodiments of the present invention can include a parabolic reflector positioned to receive light from a light source and producing a light beam; a spectral element positioned to receive the light beam from the parabolic reflector and produce a diffracted beam; and an optical detector system coupled to detect a goniospectrum from the diffracted beam. In some embodiments, the parabolic reflector can include alternating strips of reflective and non-reflective material. In some embodiments, the goniospectrophotometer can include a collimating element positioned between the parabolic reflector and the diffraction element. The collimating element can be a set of parallel plates. In some embodiments, the spectral element can be a diffraction grating. In some embodiments, the optical detector system includes a camera positioned to capture the goniospectrum. In some embodiments, the camera can be a CCD array. In some embodiments, the camera can be a digital camera. In some embodiments, the goniospectrophotometer can include focusing optics coupled between the spectral element and the detector to focus light into the camera. In some embodiments, a computer can be coupled to the optical detector system to analyze the goniospectrum detected by the optical detector system.

A method of inspecting a work piece with a goniospectrophotometer according to some embodiments of the invention includes providing an illumination light source; positioning the work piece such that a portion of the work piece is illuminated by the illumination light source; collecting scattered light from the portion of the work piece corresponding to a range of zenith angles in a parabolic reflector and forming a light beam reflected from the parabolic reflector; diffracting the light beam to form a diffracted beam; detecting a goniospectrum from the diffracted beam; determining whether the goniospectrum falls within a specification; and passing or rejecting the work piece based on the result of determining whether the goniospectrum falls within the specification. In some embodiments, providing an illumination light source includes coupling light from a lamp into an optical fiber, the optical fiber being positioned above the work piece. In some embodiments, diffracting the light beam to form a diffracted beam includes positioning a diffraction grating in the light beam. In some embodiments, detecting the goniospectrum includes measuring the diffracted beam with a position sensitive detector. The position sensitive detector can be a CCD array.

Embodiments according to the present invention provide a faster method of obtaining the color spectra versus angle of material samples or light sources for applications requiring goniospectrophotometric analyses. Methods according to the present invention apply to many other applications, such as goniometric instruments, fixed multi-angle instruments, and scatterometers with elliptical mirrors.

These and other embodiments of the invention are further described below with respect to the following figures.

In the figures, elements having the same designation have the same or similar function.

DETAILED DESCRIPTION

Some embodiments of the present invention obtain the full goniometric spectra (a goniospectrum) over an angular range greater than 90° in about 30 milliseconds. Use of parabolic reflector with the source of interest positioned at the focus of the parabola allows for simultaneous capture of data at a set of discrete angles. With this configuration, the angular light emission transforms into a collimated beam propagating parallel to the axis of the parabola. Thus, the light emanating angularly is then distributed linearly and radially with respect to the axis of the parabolic reflector along the cross-section of the reflected beam, with a quadratic one-to-one correspondence of angle and radius.

Placement of diffraction gratings or other spectrally dispersive elements in the reflected beam coupled to CCD area sensors provide for simultaneous measurement of the entire spectra for all the angles collected by the parabolic reflector. In some embodiments, a slit along the parabolic reflector can serve as an entrance aperture of the diffraction grating spectrometer. Alternatively, the parabolic reflector itself can be a thin segment of a parabola. An optional Angular Field-of-View (FOV) element can limit the angular extent of the light incident on the grating. An optional light baffle or baffles can be positioned between the source and the grating. Such a baffle can block light emanating directly from the source. In some embodiments, a collimator can be positioned between the parabolic reflector and the spectrally dispersive element. In some embodiments, a set of parallel beams where each beam corresponds to a discrete zenith angle can be produced, either by a collimator or by the parabolic reflector. The angular intensity profile is obtained by integrating the spectra at each zenith angle. Alternatively, the intensity profile can be obtained using a linear array positioned in the collimated beam space without the spectrally dispersive element.

Figure 5:
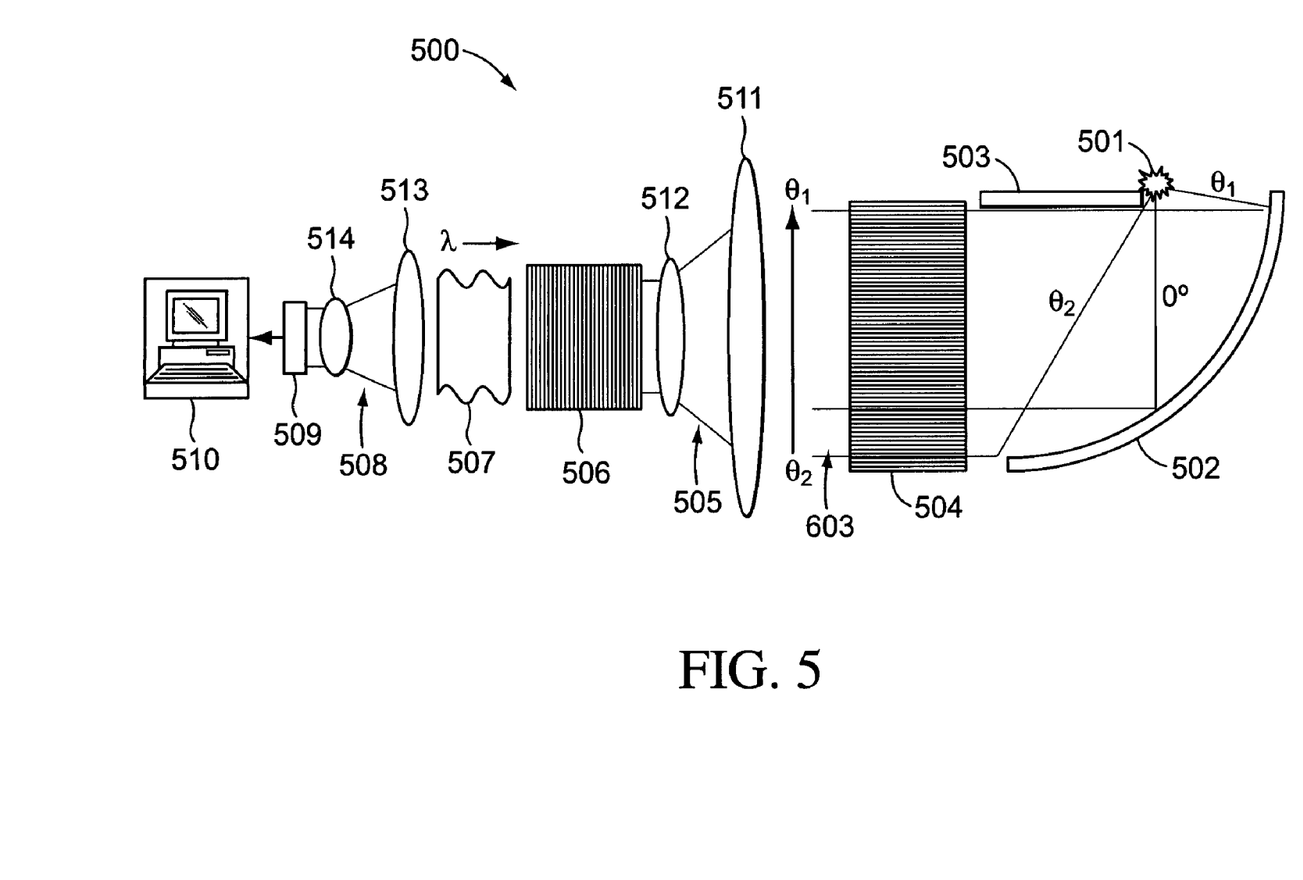
FIG. 5 illustrates a goniospectrophotometric instrument according to some embodiments of the present invention.

FIG. 5 illustrates an embodiment of goniospectrophotometer 500 according to the present invention. Light source 501 is positioned at a focus point of a parabolic reflector 502. Light source 501 can be an illumination source such as a LED, light bulb, or other light-producing source. Alternatively, light source 501 can be an illuminated material that reflects (scatters) light or fluoresces in response to an illumination beam (not shown in FIG. 5). Further, a slit (not shown) can be positioned between light source 501 and parabolic reflector 502 in order to serve as an entrance slit. Such an entrance slit can be positioned to allow light from light source 501 corresponding to the range of zenith angles θ while only allowing a narrow band of light around a particular azimuthal angle φ to enter.

Light source 501 can be oriented at an arbitrary angle, zenith and azimuthal (θ,φ), with respect to the parabola axis of parabolic reflector 502. Parabolic reflector 502 can be any parabolic shaped surface that reflects light in the wavelength range measured by goniospectrophotometer 500. In some embodiments, parabolic reflector 502 can be a segment of an off-axis parabolic mirror. Parabolic reflector 502, then, captures light corresponding to a range of zenith angles θ at a particular azimuthal angle φ.

In some embodiments, light source 501 can be formed from an illuminated sample. In some embodiments, a lamp and a multimode optical fiber bundle can be utilized to deliver the illumination beam to the sample to produce light source 501. In some embodiments, a 2.4 mm diameter fiber bundle with individual component fibers of nominally 40 µm diameter with numerical aperture of about 0.55 can be utilized to deliver light to a material to form light source 501. Light from a high intensity tungsten filament lamp driven by a DC power supply or light from a high intensity pulsed Xenon flashlamp can be coupled into the optical fiber. Any other lamp may be utilized, depending on the range of optical wavelengths that are under investigation.

Light emanating from light source 501 between the zenith angles $\theta_1$ and $\theta_2$ is subtended by parabolic reflector 502. Further, parabolic reflector 502 can be set at particular azimuthal angles. In some embodiments, parabolic reflector 502 may intersect zenith angles of $|\theta_2-\theta_1|$ greater than 90°, but parabolic reflectors intersecting less of a spread of azimuthal angles can also be utilized. In some embodiments, parabolic reflector 502 can be set at a set of azimuthal angles as well. In some embodiments of the invention, parabolic reflector 502 may include slit apertures or otherwise narrow strips of reflective material to reflect light at particular discrete zenith angles between the angles $\theta_1$ and $\theta_2$. In some embodiments, parabolic reflector 502 can be a continuous reflector, reflecting light corresponding to all angles in the range of zenith angles $\theta_1$ to $\theta_2$. In some embodiments, parabolic mirror 502 can be thin so as to collect light only from a narrow range of azimuthal angles around a predetermined azimuthal angle φ. In some embodiments, parabolic reflector can be formed in a replication process from an originally machined part.

Figure 6:
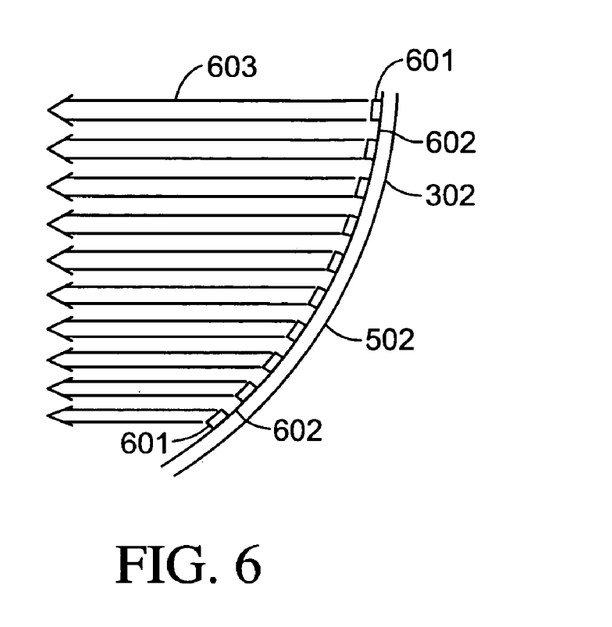
FIG. 6 illustrates an embodiment of a parabolic reflector that can be utilized in embodiments of the present invention.

FIG. 6 illustrates a cross-section of a portion of parabolic reflector 502 according to some embodiments of the present invention. The embodiment of parabolic reflector 502 shown in FIG. 6 includes reflective regions 601 and non-reflective regions 602. Nonreflective regions can be absorbing strips on parabolic reflector 502 or may be slits formed in parabolic reflector 502. Light beam 603 originate by reflection from light source 501, then, can include a set of discreet light beams with each beam in the set of discreet light beams corresponding to light collected at a corresponding particular zenith angle $\theta_n$. Light from light source 501 are reflected from parabolic mirror 502 substantially in parallel rays of light with each ray of light associated with light emanating from light source 501 at a corresponding zenith angle from light source 501. In some embodiments, about five to about eight zenith angles of data can be taken, which is consistent with the ASTM Draft Standard WK1164 for measurement of gonioapparent materials. Light beam 603 reflected from parabolic reflector 502, then, can be in the form of pseudo-collimated thin rays of light, each ray corresponding to a different unique zenith angle between the angles of $\theta_1$ and $\theta_2$. Some embodiments of parabolic reflector 302 provide for a continuous beam 603 where light emitted at a particular zenith angle $\theta_n$ corresponds to a particular position in light beam 603.

In some embodiments, parabolic reflector 502 can have a focal dimension of about 10 mm. In general, however, parabolic reflector 502 can have any focal dimension. With a 10 mm focal dimension, light source 501 can have a lateral extent of about 1 mm and maintain angular resolution to a few degrees. In operation, light source 501 is positioned at a focus of parabolic reflector 502.

Figure 7:
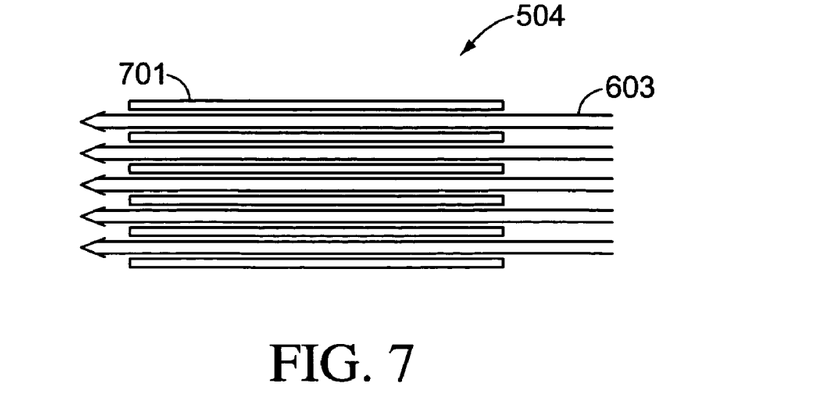
FIG. 7 illustrates an embodiment of a collimator that can be utilized in embodiments of the present invention.

In some embodiments of the invention, beam 603 reflected from parabolic reflector 502 can be further collimated by collimator 504 shown in FIG. 5. As shown in FIG. 7, in some embodiments, collimator 504 can be a mechanical array of thin plates 701 separated by spacers (not shown) that further narrow the view. In some embodiments, collimator 504 can include any arrangement of alternating transparent and reflective surfaces that further collimates light beam 603. In embodiments where beam 603 includes a set of discrete light beams, collimator 504 can include a corresponding set of parallel plates. In some embodiments, where beam 603 is a continuous beam, collimator 504 may include a set of parallel plates so that beam 603 exciting collimator 504 includes a set of discrete beams. In some embodiments, collimator 504 can include a pair of plates to collimate beam 603 as a whole.

Further, in some embodiments a light baffle 503 (FIG. 5) can be fixed adjacent light source 501 to block light from light source 501 that is outside the range of azimuthal angles between $\theta_1$ and $\theta_2$ from entering collimator 504. In embodiments where a continuous beam 603 is utilized, collimator 504 is absent.

With continuing reference to FIG. 5, beam 603, which may or may not include discrete beams, is directed onto spectral element 506. Spectral element 506 can be any device that spectrally disperses light in beam 603.

In some embodiments, focusing optics 505 can be introduced to direct light beams 603 onto spectral element 506. In some embodiments, focusing optics 505 can be cylindrical beam-shaping optics that reduce the linear extent of the parallel light beams prior to incidence upon spectral element 506. In some embodiments, focusing optics 505 can include a focusing lens 511 followed by a collimating lens 512.

Figure 8A:
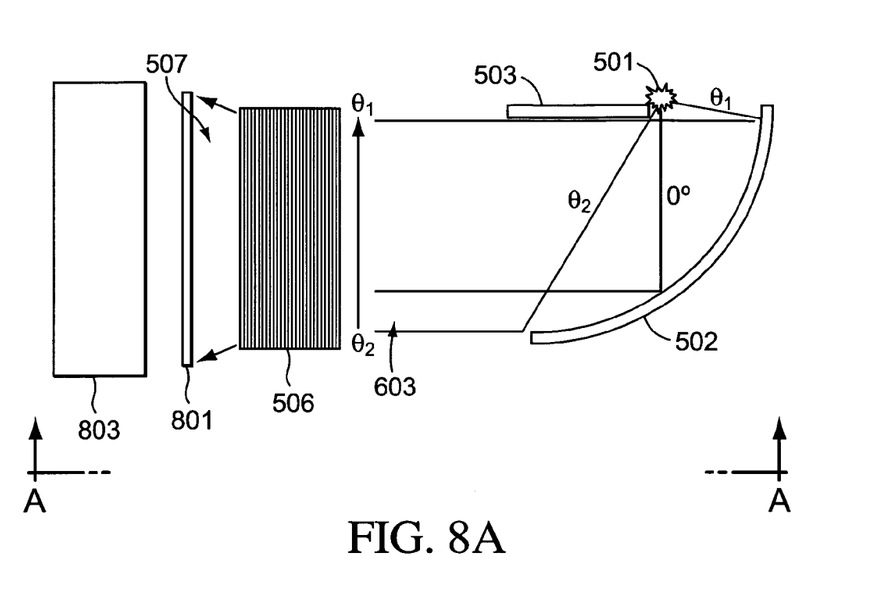
FIG. 8A illustrates a cross sectional view of an embodiment of goniospectrophotometer according to the present invention.
Figures 8B, 8C:
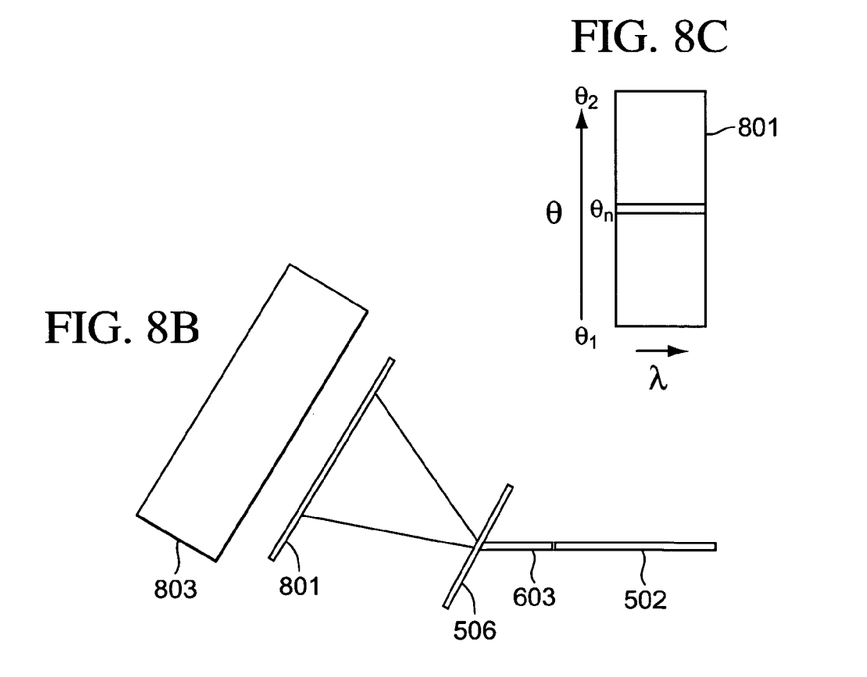
FIG. 8B illustrates a cross section view along the AA direction shown in FIG. 8A of an embodiment of a goniospectrophotometer according to the present invention.
FIG. 8C illustrates a sample goniospectrum detected by a detector in an embodiment of a goniospectrophotometer according to the present invention.

Spectral element 506 can include any device that separates a light beam into its respective wavelengths, for example a diffraction grating or a prism. In some embodiments, a diffraction grating having a transmission grating with 1500 lines/mm optimized for maximum efficiency over a spectral range of from about 360 to about 800 nm is utilized. Typically, light beam 603 is diffracted by spectral element 506 into multiple orders of spectra. The goniospectral distribution can then be determined by measuring the light intensity over one order of diffraction of beam 603. The diffracted beam from spectral element 506 is shown in FIG. 5 as spectra 507. Spectra 507 includes all of the orders of diffraction. FIG. 8C illustrates an embodiment of goniospectrophotometer according to the present invention that utilizes the zero'th order diffraction. One skilled in the art will recognize that a goniospectrum can also be obtained from higher diffraction orders.

With reference to FIG. 5, the light from a single order of diffraction in spectra 507 can be collected by lens system 508 and directed onto a detector 509. Lens system 508, when present in embodiments of goniospectrophotometer 500, can include a focusing lens 513 followed by a collimating lens 514.

Detector 509 can be any spatially sensitive detective device, for example a charge-coupled detector (CCD) array. In some embodiments, such as, for example, that shown in FIG. 8, the spectra can be projected onto a screen 801 before being detected by detector 509. Other spatially sensitive light detectors can also be utilized, such as, for example, a CMOS camera or Vidicon camera. The signals from detector 509, which can be either analog or digital depending on the particular detector system, are then input to an analyzer or computer system 510. Computer system 510 then provides the goniospectrum from the data collected for recordation, further processing, or display.

FIG. 8A illustrates a cross-sectional view of goniospectrophotometer 800 according to some embodiments of the present invention. As described with FIG. 5, light from light source 501 corresponding to a range of zenith angles $\theta_1$ to $\theta_2$ is captured by parabolic reflector 502 and directed into beam 603. As before, beam 603 can be a continuous beam or a discrete set of beams with each separate beam corresponding to a discrete zenith angle $\theta_n$. In a continuous beam, light from zenith angle $\theta_n$ can be detected by position in the beam.

Beam 603 is incident on spectral element 506, which in FIG. 8A is a diffraction grating with rulings parallel to the plane of the cross section shown in FIG. 8A. The diffracted beam 507 is then displayed on screen 801 and detected by detector 803. In FIG. 8A, spectral element 506 is illustrated so as to show the direction of the rulings on a diffraction grating. Spectral element 506 would, in this plane of reference, be oriented such that light beam 603 is incident directly on the surface of spectral element 506.

FIG. 8B illustrates a perpendicular cross section of goniospectrophotometer 800 along the direction AA shown in FIG. 8A. A slice of beam 603 corresponding to zenith angle $\theta_n$ is shown being diffracted from parabolic reflector 502. In this plane, the diffraction grating of spectral element 506 is set at an angle with respect to beam 603. The rulings of the diffraction grating are perpendicular to the cross sectional plane of goniospectrophotometer 800 shown in FIG. 8B. The zero'th order spectra of the diffracted beam 507 corresponding to zenith angle $\theta_n$ is displayed on screen 801. A detector 803, which can be a digital camera such as a CCD camera, then detects the spectra corresponding to zenith angle $\theta_n$.

FIG. 8C illustrates a full set of spectra, a goniospectrum, projected on screen 801. The intensity of light is illustrated, for an example goniospectrum, by the shading. Detector 803, then, can simultaneously measure the spectra as a function of zenith angle for all zenith angles in the range $\theta_1$ to $\theta_2$ in a single exposure. Each slice in the wavelength direction corresponds to a single zenith angle $\theta_n$ (or more accurately a small set of angles $\Delta\theta$ around $\theta_n$). Therefore, the spectra for any particular angle can be determined, as is illustrated by the slice indicating the spectrum at zenith angle $\theta_n$ shown in FIG. 8C.

In some embodiments, camera 803 can be a 12-bit digital CCD camera with a 1037×1376 array of 6.45 µm square pixels. The CCD image can be acquired in a computer system 510 operating a digital frame grabber software such as the Beam Profiler Software produced by Photon, Inc. In some embodiments, the image acquisition time is about 90 ms, based on the maximum rate of the digital frame grabber.

In some embodiments, the image captured by the digital frame grabber software can be exported to analysis software, for example MatLab, for analysis. Data analysis can involve, for example, determination of material reflectance versus angle, or transformation of angular spectral data to CIE colorimetric spaces. In some embodiments, computer 510 may only check the goniospectrum to insure that it falls within a particular manufacturing specification. In which case, computer 510 may alert an operator if the goniospectrum falls outside of the predetermined specification.

Figure 9:
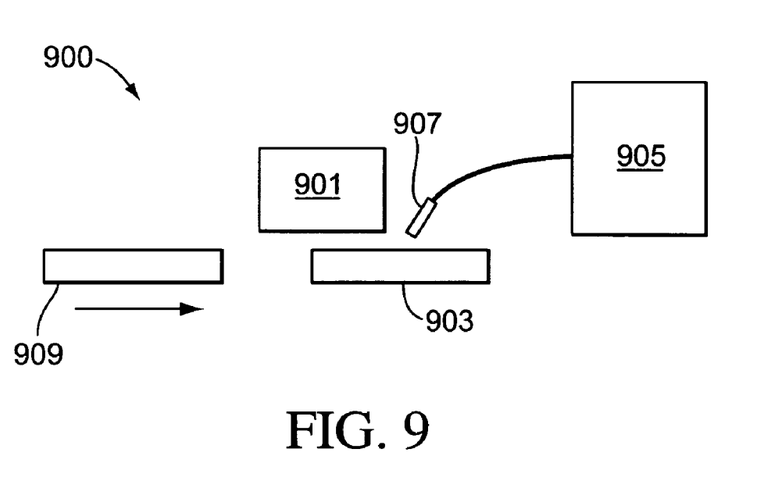
FIG. 9 illustrates utilization of a goniospectrophotometer according to some embodiments of the present invention in a production process.

FIG. 9 illustrates utilization of goniospectrophotometer 901 according to some embodiments of the present invention in a manufacturing environment 900. As shown in FIG. 9, a source of light 905 is coupled into an optical fiber 907 so that a work piece 903 can be illuminated. Goniospectrophotometer 901 is positioned such that a goniospectrum of scattered light from work piece 903 is obtained. In some embodiments, several goniospectra at differing positions on work piece 903 can be obtained. Goniospectrophotometer 901, then, determines whether the goniospectrum obtained falls within a predetermined specification and then passes or rejects work piece 903 based on that determination.

Work piece 903 can be any part where a goniospectrum is an important parameter, for example the coloration, paint coverage, or other characteristic. Further, work piece 903 may be on an assembly line and therefore is followed by another work piece 909 once work piece 903 has been inspected.

Embodiments of goniospectrophotometer, as described herein, provide for faster and cheaper acquisition of goniometric spectra. Spectral data for each of a set of zenith angles around light source 501 are taken in a digital camera, which also captures each spectrum from each of the set of zenith angles simultaneously. Therefore, embodiments of the goniospectrophotometer according to the present invention can utilize only a single digital camera or CCD detector and can take simultaneous spectra in the time it takes for data acquisition by the single camera.

The embodiments described in this disclosure are examples only and are not intended to be limiting. As such, the invention is limited only by the following claims.

I claim:

1. A method of obtaining a goniospectrum, comprising:
parabolically reflecting light from a light source positioned at the focus of a parabolic mirror to provide a beam of light, the beam of light including parallel light corresponding to a range of zenith angles at a particular azimuthal angle from the light source, wherein a position of the parallel light in the beam of light corresponds to one zenith angle of the range of zenith angles;
spectrally dispersing light from the beam; and capturing the goniospectrum of the light source corresponding to the beam in a form that can be communicated to a user, the goniospectrum including spectra corresponding to the range of zenith angles simultaneously.

2. The method of claim 1, wherein the beam of light includes a set of discrete beams, each beam in the set of discrete beams corresponding to a zenith angle in the range of zenith angles.

3. The method of claim 2, further including collimating the set of discrete beams.

4. The method of claim 1, wherein spectrally dispersing light from the light beam includes diffracting the light beam in a diffraction grating.

5. The method of claim 1, further including focusing the beam before spectrally dispersing the light from the beam.

6. The method of claim 1, wherein capturing a goniospectrum includes detecting a spectrum from the diffraction grating corresponding a plurality of zenith angles within the range of zenith angles.

7. The method of claim 6, wherein the spectrum is a zero'th order spectrum.

8. The method of claim 6, wherein the spectrum is a higher order spectrum.

9. The method of claim 6, wherein the spectrum from the diffraction grating is projected on a screen.

10. The method of claim 6, wherein detecting the spectrum includes digitally capturing an image of the spectrum in a digital camera.

11. The method of claim 10, wherein the digital camera is a CCD camera.

12. The method of claim 1, wherein the light source is a sample illuminated by an illumination beam.

13. The method of claim 12, wherein the illumination beam results from a source of light coupled to the same through an optical fiber.

14. A goniospectrophotometer, comprising:
a parabolic reflector to receive light from a light source positioned at its focus, the parabolic reflector producing a parallel light beam where each position in the parallel light beam corresponds to a zenith angle of a range of zenith angles around the light source at a selected azimuth angle;
a spectral element positioned to receive the light beam from the parabolic reflector and produce a diffracted beam; and
an optical detector system coupled to simultaneously detect a goniospectrum of the light source from the diffracted beam.

15. The goniospectrophotometer of claim 14, wherein the parabolic reflector includes alternating strips of reflective and non-reflective material.

16. The goniospectrophotometer of claim 14, further including a collimating element positioned between the parabolic reflector and the diffraction element.

17. The goniospectrophotometer of claim 16, wherein the collimating element is a set of parallel plates.

18. The goniospectrophotometer of claim 14, wherein the spectral element is a diffraction grating.

19. The goniospectrophotometer of claim 14, wherein the optical detector system includes a camera positioned to capture the goniospectrum.

20. The goniospectrophotometer of claim 19, wherein the camera is a CCD array.

21. The goniospectrophotometer of claim 19, wherein the camera is a digital camera.

22. The goniospectrophotometer of claim 14, further including focusing optics coupled between the parabolic reflector and the spectral element.

23. The goniospectrophotometer of claim 14, further including focusing optics coupled between the parabolic reflector and the spectral element.

24. The goniospectrophotometer of claim 14, further including a computer coupled to the optical detector system to analyze the goniospectrum detected by the optical detector system.

25. A goniospectrophotometer, comprising:
means for capturing light from a light source at a range of zenith angles for an azimuthal angle and providing a parallel light beam where each position in the parallel light beam corresponds to a zenith angle in the range of zenith angles;
means for spectrally dispersing light in the light beam; and
means for simultaneously capturing a goniospectrum corresponding to the range of zenith angles.

26. A method of inspecting a work piece, comprising:
providing an illumination light source;
positioning the work piece such that a portion of the work piece is illuminated by the illumination light source;
collecting scattered light from the portion of the work piece corresponding to a range of zenith angles in a parabolic reflector and forming a light beam reflected from the parabolic reflector;
diffracting the light beam to form a diffracted beam;
detecting a goniospectrum from the diffracted beam;
determining whether the goniospectrum falls within a specification; and
passing or rejecting the work piece based on the result of determining whether the goniospectrum falls within the specification.

27. The method of claim 26, wherein providing an illumination light source includes coupling light from a lamp into an optical fiber, the optical fiber being positioned above the work piece.

28. The method of claim 26, wherein diffracting the light beam to form a diffracted beam includes positioning a diffraction grating in the light beam.

29. The method of claim 26, wherein detecting the goniospectrum includes measuring the diffracted beam with a position sensitive detector.

30. The method of claim 29, wherein the position sensitive detector is a CCD array.

* * * * *